United States Patent [19]

Ghiara

[11] Patent Number: 5,985,243
[45] Date of Patent: Nov. 16, 1999

[54] **MOUSE MODEL FOR *HELICOBACTER PYLORI* INFECTION**

[75] Inventor: Paolo Ghiara, Siena, Italy

[73] Assignee: Chiron S.p.A., Siena, Italy

[21] Appl. No.: 08/649,604

[22] PCT Filed: Aug. 18, 1995

[86] PCT No.: PCT/IB95/00710

§ 371 Date: May 24, 1996

§ 102(e) Date: May 24, 1996

[87] PCT Pub. No.: WO96/09757

PCT Pub. Date: Apr. 4, 1996

[30] Foreign Application Priority Data

Sep. 28, 1994 [GB] United Kingdom .................... 9419661
Mar. 28, 1995 [GB] United Kingdom .................... 9506251

[51] Int. Cl.⁶ ............................. A61K 49/00; C12N 5/00
[52] U.S. Cl. ................................. 424/9.2; 800/9
[58] Field of Search ................................. 800/2, DIG. 4, 800/5; 435/243, 252.1; 424/9.2

[56] References Cited

U.S. PATENT DOCUMENTS 5,625,124  4/1997  Falk et al. .................................... 800/2

FOREIGN PATENT DOCUMENTS

WO 90/14837  12/1990  WIPO.

OTHER PUBLICATIONS

M Karita et al (1994) American J Gastroenterology 89: 208–213.
L Marzio et al (1994) Gastroenterology 106: A129.
M Karita (1991) American J Gastroenterelogy 86: 1596–1603.
P Ghiara et al. (1994) American Journal of Gastroenterology 89: 1319, abstracts 136 and 137.
K Saukkonen (1988) Microbial Pathogenesis 4: 203–211.
L–T Hu et al. (1992) Infection and Immunity 60: 2657–2666.
Webster's Ninth New Collegiate Dictionary (1990) p. 877.
G Audesirk et al (1986) Biology Life on Earth pp. 355–357, 367.
Blaser, "Gastric Campylobacter–like Organisms, Gastritis, and Peptic Ulcer Disease", *Gastroenterology*, 1987, 93, 371–383.

Ghiara et al., "Infection by *Helicobacter pylori* in a mouse model that mimics human disease: protection by oral vaccination", *GUT,* 1995, Abstract No. 204.
Ghiara et al., "Colonization of Murine Stomach by Fresh Isolates of *Helicobacter Pylori*", *Am. J. Gastroenterol.,* 1994, 89(8), 1319, Abstract No. 137.
Hu et al., "Purification of Recombinant *Helicobacter pylori* Urease Apoenzyme Encoded by ureA and ureB", *Infect. Immunity,* 1992, 60(7), 2657–2666.
Karita et al., "New Small Animal Model for Human Gastric *Helicobacter pylori* Infection: Success in Both Nude and Euthymic Mice", *Am. J. Gastroenterology,* 1991, 86(11), 1596–1603.
Karita et al, "Establishment of a Small Animal Model for Human *Helicobacter pylori* Infection Using Germ–Free Mouse", *Am. J. Gastroenterology,* 1994, 89(2), 208–213.
Marchetti et al., "Development of a mouse model of *Helicobacter pylori* infection that mimics human disease", *Science,* 1995, 267(5207), 1655–1658.
Marzio et al., "Gastric Ulcer and Antral Gastritis Experimentally Induced by Human *Helicobacter Pylori* in Bacillary and Coccoid Form in Balb/C Euthymic Mice", *Gastroenterology,* 1994, 106(4), A129.
Matsumoto et al., "Metronidazole resistant mutant isolated from *H. pylori* infected euthymic mice model", *GUT,* 1995, 37, A49.
Megraud, "Epidemiology of *Helicobacter Pylori* Infection", *Gastroenterol. Clin. North Am.,* 1993, 22, 73–88.
Rappuoli et al., "Pathogenesis of *Helicobacter pyroli* and perspectives of vaccine development against an emerging pathogen", *Behring Institute Mitteilungen,* 1994, 95, 42–48.
Rappuoli et al., "Development of a vaccine against *Helicobacter pylori*: a short overview", *Eur. J. Gastroenterol. Hepatol.,* 1993, 5(Supp. 2), S76–S77.
Saukkonen, "Experimental meningococcal meningitis in the infant rat", *Microb. Pathogenesis,* 1988, 4, 203–211.
Taylor et al., "The Epidemiology of *Helicobacter pylori* Infection", *Epidemiol. Rev.,* 1991, 13, 42–59.

*Primary Examiner*—Bruce R. Campell
*Attorney, Agent, or Firm*—Woodcock Washburn Kurtz et al.; Alisa A. Harbin; Robert P. Blackburn

[57] ABSTRACT

A mouse model for *Helicobacter pylori* infection prepared by infecting a euthymic mouse with a dose of bacteria freshly isolated from an infected human.

5 Claims, 2 Drawing Sheets

FIG. 1A
FIG. 1B
FIG. 1C
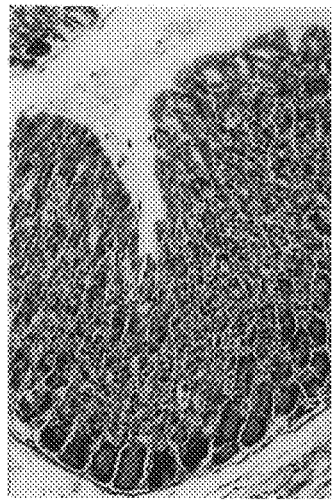
CONTROL MOUSE
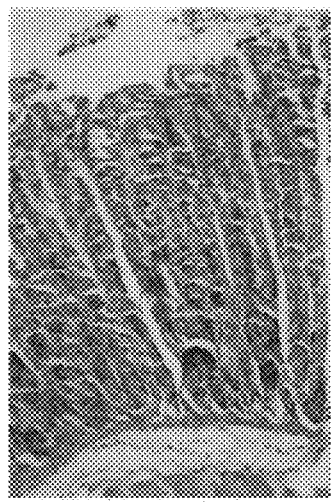
MOUSE INFECTED
WITH SPM314 STRAIN
FOR 8 WEEKS
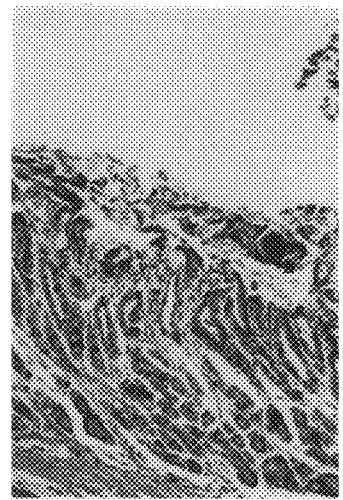
MOUSE INFECTED
WITH SPM326 STRAIN
FOR 8 WEEKS

MOUSE MODEL FOR *HELICOBACTER PYLORI* INFECTION

The present invention relates to a murine model for human infection by *Helicobacter pylori* (*H.pylori*). The model is especially useful for the development of vaccines against *H. pylori*.

BACKGROUND OF THE INVENTION

*Helicobacter pylori* was isolated in 1982 by B. Marshall and J. Warren using microareophilic conditions that had been developed to grow *Campylobacter jejuni*. *H. pylori* bacteria are S-shaped, gram negative bacilli 2–3.5 μm in length and 0.5–1 μm in width. The cell wall is smooth and adheres closely to the cytoplasmic membrane. *H. pylori* is responsible for the most common infection in the world. In developing countries 80% of the population is infected by the bacterium at the age of 20, while in developed countries *H. pylori* infection increases with age from <20% in 30-year old people to >50% in 60-year olds (Megraud, Gastroentrol. Clin. North Am., 1993, 22, 73–88; Taylor and Blaser, Epidemiol. REv., 1991, 13, Graham, J. Gastroenterol. Hepatol., 1991, 6, 105–113). The bacterium is probably transmitted by the oral-fecal route. Presently, there are two theories to explain the acquisition of *H. pylori*. One states that infection occurs during the first years of life and persists forever (cohort effect). The other purports that the acquisition of infectious bacteria occurs continuously, at a rate of 0.5–2% per year and, once established, the infection is chronic, possibly permanent. Risk factors for infection are crowding, poor hygiene and host-specific genetic factors.

Colonization of the mucosa of the stomach and the duodenum by *Helicobacter pylori* is today recognized as the major cause of acute and chronic gastroduodenal pathologies in humans (Blaser, Gastroenterology, 1987, 93, 371–383). The recognition of the infectious nature of the illness is having a major impact in the treatment of the disease that is shifting from the treatment of symptoms by anti-H2 blockers to the eradication of the bacterial infection by antibiotic regimen.

In spite of the unquestionable successes that will be achieved with antibiotic treatment, it should be remembered that this inevitably leads to the occurrence of resistant strains that in the long term will make antibiotics ineffective. This suggests that vaccination, which classically is the most effective way to prevent and control infectious diseases in a large population, could be used to prevent infection and possibly also to treat the disease (Rappuoli et al., J. Gastroenterol. Hepatol., 1993, 5 (Suppl. 2), 76–78).

Vaccine development requires understanding of a number of critical steps that are not yet fully studied. These are:

1) identification of the factors important for virulence,
2) large-scale production and characterization of the virulence factors,
3) development of appropriate animal models to test the virulence and immunogenicity of the molecules identified,
4) development of an antigen delivery system capable to induce the type of immunity that is necessary to confer protection against infection and disease.

One of the most pressing needs is the development of an animal model in which to study *H. pylori* infection. Gnotobiotic piglets and beagle dogs can be artificially infected by *H. pylori*. In adult humans chronic *H. pylori* infection is associated with infiltration with neutrophils and mononuclear cells, whereas in infected children the lamina propria is infiltrated mainly by lymphocytes. Gnotobiotic piglets and dogs infected with *H.pylori* have a gastritis that is much more similar to the response seen in children with the inflammatory infiltration consisting mainly of lymphoplasmacytic cells with very few neutrophils. Thus these two infection models can only reproduce a pathological picture observed in a limited percentage of human patients. Non human primates have been reported to be naturally infected by *H.pylori*; the gastritis observed is more similar to that observed in the infected adult humans. Nonetheless, no evidence of *H.pylori*-dependent peptic ulceration has been reported in this animal model. A major problem with *H.pylori* infection of gnotobiotic pigs, dogs and monkeys is also the fact that these models are very expensive and have special housing requirements.

An animal model has been established by infecting germ-free mice with *Helicobacter felis*. The infection is characterized by an inflammatory response mostly consisting of neutrophil and eosinophil infiltration. However, *H.felis* lacks both cagA and vacA genes, is not adherent to epithelial cells and even a persistent infection of the mouse gastric mucosa does not give rise to ulcerations. Thus the *H.felis* model of infection in the mouse cannot give any direct information relating to *H.pylori*-specific pathogenic determinants. *H.felis* has also been reported to infect the gastric mucosa of dogs where it induces a cell infiltrate mainly consisting of mononuclear lymphocytes.

*H. mustalae* natural infection of North American ferrets causes chronic inflammation to the host. *H. mustalae* infection is often associated with ulcers but this bacterium does not synthesize a vacuolating cytotoxin. Moreover, the use of this model may not be easily available to most laboratories.

*Gastrospirillum hominis*, now re-named *H. heilmanii*, has been found associated with gastric mucosae of many domestic animals. It has also occasionally been found in human gastric biopsies associated with gastritis, and can successfully colonize the laboratory mouse stomach. Of course, reliable mouse models would be preferred by most researchers in the field.

Recently, Karita et al. have described successful gastric colonisation of athymic nude mice and germ-free euthymic mice by isolates of *H.pylori* derived from human gastric mucosa (Karita et al., Am J. Gastroenterol. 86, 1596–1603, 1991; Ibid 89, 208–213, 1994). From the model of Karita, however, it is apparent that both the immunological system and the normal gastric flora of the mouse stomach have far-reaching effects on infection by *H.pylori*. Indeed, in euthymic mice the level of infection observed was far lower than in athymic mice. Moreover, non-germ-free mice proved impossible to infect on a permanent basis. Since *H.pylori* injects humans with functional immunological systems and normal gastrointestinal flora, the important effects of both of these factors must be taken into account in the development of an animal model. A euthymic mouse with normal intestinal flora which can be successfully infected by *H.pylori* would therefore be the ideal model.

SUMMARY OF THE INVENTION

The present invention describes the development of a mouse model for *H.pylori* infection wherein euthymic mice can be successfully infected by fresh isolates of *H.pylori* obtained directly from human patients. The infected mice develop a gastric pathology similar to that observed in humans. Moreover, the mice have been observed to be capable of developing an immunity to *H.pylori* infection when immunised with a suitable immunogen.

BRIEF DESCRIPTION OF THE DRAWINGS

FIGS. 1A–1C shows the histological (H&E stained) appearance of mouse gastric mucosa after infection with non-toxic strain SPM314 and toxic strain SPM326, together with an uninfected control.

DETAILED DESCRIPTION OF THE INVENTION

Figure 2:
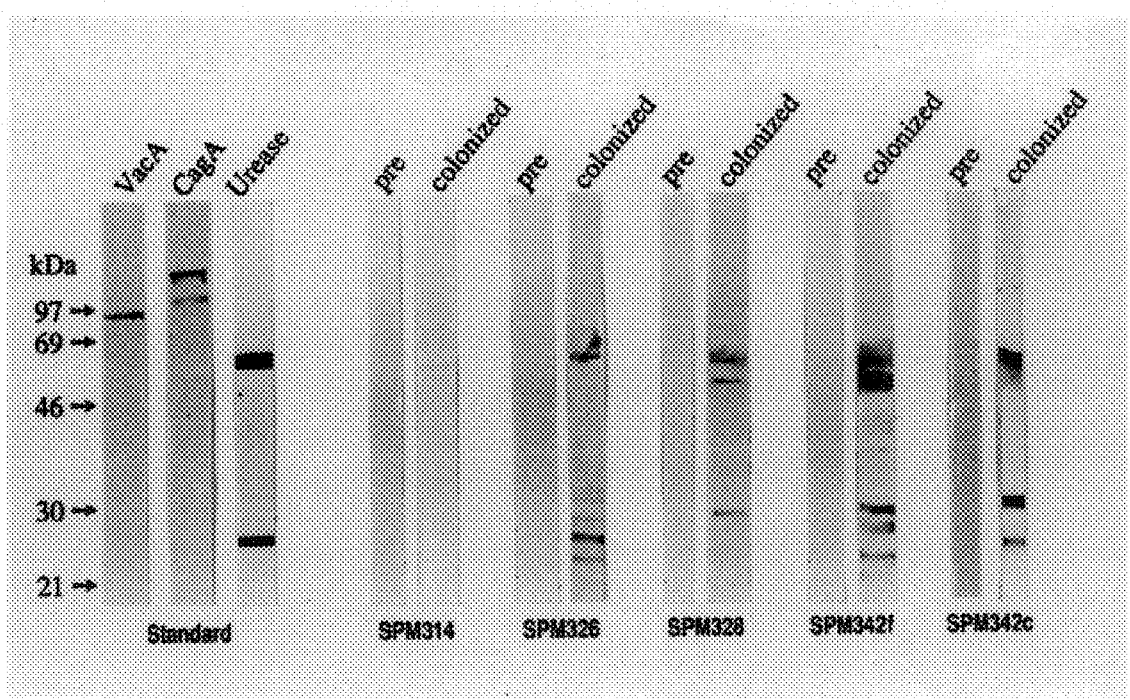
FIG. 2 is a Western blot showing the reaction of sera from mice to whole cell extracts of *H.pylori*. An immune response in the mice is apparent in the 4th week of colonisation by *H. pylori*.

According to a first aspect of the present invention, therefore, there is provided a method for infecting a euthymic mouse with a human isolate of *Helicobacter pylori* comprising the steps of:

1) isolating *Helicobacter pylori* from a human patient; and
2) administering a dose of the fresh isolate of *Helicobacter pylori* to a euthymic non-germ-free mouse.

By "fresh isolate", it is intended to refer to *H.pylori* which has been isolated from human patients and not passaged in the laboratory in any way. Thus, the bacteria isolated from the patient are the bacteria used to infect mice.

In contrast, Karita et al. have used established strains of *H.pylori*, isolated from human patients and then maintained in the laboratory. It is postulated that such *H.pylori* cultures have a reduced virulence and are thus unable to infect euthymic non-germ-free mice.

CD1 mice (both specific pathogen free and conventional outbred mice), BALB/c (both specific pathogen free and conventional inbred mice) and C57BL/6 inbred specific pathogen free mice have been tested and found to be useful in the infection model, illustrating the broad applicability of the technique.

Preferably, the mice are non-germ free mice.

Using the method of the invention, special procedures are not required to infect the mice. Infection is accomplished orally through a gastric gavage. Preferably, $10^9$ CFU of *H.pylori* is administered. The administration is advantageously repeated at 3 and 6 days from the initial infection.

Preferably, the mice to be infected are starved for 24 hours prior to infection. Before each infection, stomach acid is advantageously neutralised, for example by oral administration of $NaHCO_3$.

It has been found that the infectivity of the *H.pylori* isolates is improved by passaging in mice. Thus, *H.pylori* isolated from mice infected according to the invention are better adapted to murine hosts and can re-infect mice with even greater efficiency than the original isolate.

Accordingly, the invention provides a method for infecting a euthymic mouse with *H.pylori* comprising the steps of 1) isolating *H.pylori* from a mouse infected in accordance with the first aspect of the present invention; and
2) infecting a euthymic, non-germ-free mouse with the *H.pylori* isolate.

Preferably, the mice are non-germ free mice.

Moreover, the invention provides *H.pylori* isolates from a mouse in accordance with the first aspect of the invention. Such an isolate is useful in the generation of further *H.pylori* infected mice.

It has been found that *H.pylori* isolates obtained from humans or mice may be stored for brief periods in the laboratory if the isolates are frozen immediately.

The invention further provides a euthymic, preferably non-germ-free, mouse injected with *H.pylori*.

Mice according to the invention are useful in the study of the pathogenesis, treatment and prevention of *H.pylori* infection.

A preferred use for the mice of the invention is the development of vaccines for use in the prevention and/or treatment of *H.pylori* infection and diseases associated therewith. The invention therefore encompasses the use of mice according to the invention for vaccine development.

Such vaccines may either be prophylactic (to prevent infection) or therapeutic (to treat disease after infection).

Such vaccines comprise antigen or antigens, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, *H.pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) those formulations described in PCT Publ. No. WO 90/14837, including but not limited to MF59 (containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.)), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-1-alanyl-d-isoglutamine (nor-MDP), N-acetylmuramyl-1-alanyl-d-isoglutaminyl-1-alanine-2-(1'-2'-dipalmitoyl-sn-glycero-3-huydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection-may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

Moreover, there is provided a method for evaluating a vaccine against *H.pylori* comprising the steps of:

1) administering to a euthymic, preferably non-germ-free, mouse an effective amount of a candidate vaccine;
2) infecting the mouse in accordance with the present invention; and
3) observing the incidence of *H.pylori* infection in the mouse.

As will be apparent to one of the ordinary skill in the art, the therapeutic as well as the prophylactic effect of vaccines may be evaluated by the method of the invention, by reversing steps 1 and 2 above.

EXPERIMENTAL

Isolation of Strains and Characterization of Phenotype

Human gastric biopsies of HP positive patients were streaked onto blood agar plates and bacterial strains were isolated following commonly used procedures. Strains were grown under microaerophilic conditions and their phenotype was characterized as to type by western blot analysis, using anti CagA or anti VacA sera, and by assessment of vacuolating activity on a HeLa cell line HP CCUG 17874 type strain that was obtained from the University of Goteborg and cultured in the same conditions as the fresh isolates. Table 1 summarizes the phenotypic characterization of HP strains used in this study.

TABLE I

| STRAIN | Strain phenotype | |
|--------|---------|---------|
|        | VacA (WB) | CagA (WB) |
| SPM292 | − | − |
| 314    | − | − |
| 328    | − | + |
| 342C   | − | + |
| 342F   | + | + |
| 326    | + | + |
| CCUG   | + | + |

All the HP strains were harvested from the plates using a sterile cotton swab and suspended in sterile saline, the suspension kept on ice for up to 20 mins before being administered orally to the mice.

Inoculation Protocol 6 week old CD1/SPF and BALB/C mice were purchased from Charles River (Calco, Italy) and housed in animal facilities with a 12 h light-dark schedule (illumination: 07:00 h to 19:00h). Animals had free access to sterile water and food but were fasted for 24 h before each treatment as well as before killing. Mice were given 0.25 ml of 0.2M $NaCHO_3$ orally through a gastric gavage to neutralize acidity 30 mins before receiving $10^9$ CFU of each HP strain in 0.15 ml of sterile saline administered through the same route. The same treatment was repeated after 3 and 6 days.

Assessment of Colonization 1, 2, 4 and 8 weeks after the beginning of the oral treatments groups of 4 mice were bled and killed by cervical dislocation. The stomachs were harvested and opened through the lesser curvature. The forestomach, containing non-mucosal epithelial squamous tissue was eliminated. Approximately ⅓ of the gastric tissue, including oxyntic and fundic mucosa was cut off, fixed in 4% buffered formalin, embedded in paraffin and processed for histology following common procedures.

The remaining tissue was streaked onto Skirrow's sheep blood agar plates that were subsequently incubated for 3 days at 37° C. under microaerophilic conditions. Growing bacteria were identified as HP on the basis of Gram staining and the production of urease and catalase.

The immune response against the colonizing HP strain was assessed by means of serum activity in western blot analysis using a whole cell preparation of the inoculated strain as antigen.

Immunization Protocol and Challenge with Strain SPM292

6 week old male CD1/SPF mice were immunized orally at days 0, 7, and 14 with 0.5 ml of saline alone or containing 10 μg of LT (Heat labile toxin of Enterotoxigenic *E.coli*) with or without 100 μg of purified Urease from HP strain CCUG17874. At day 21 all the mice were challenged orally with $10^9$ CFU of SPM292 as described above; the challenge was repeated after 3 and 6 days. Two weeks afterwards, mice were killed and colonization was assessed as described above.

RESULTS Table II summarizes the results of colonization experiments.

TABLE II

| | CD1/SPF | | | | |
|---|---|---|---|---|---|
| | INFECTED/TOTAL | | | | |
| Strain | Week 1 | Week 2 | Week 4 | Week 8 | Cumulative |
| None | 0/4 | 0/5 | 0/5 | 0/6 | 0/20 |
| SPM292 | 1/4 | 2/4 | 4/4 | 4/4 | 11/16 |
| SPM314 | 1/4 | 2/4 | 4/4 | 4/4 | 11/16 |
| SPM328 | 3/4 | 4/4 | 4/4 | 4/4 | 15/16 |
| SPM342C | 2/4 | 3/4 | 4/4 | 4/4 | 13/16 |
| SPM342F | 4/4 | 4/4 | 4/4 | 4/4 | 16/16 |
| SPM326 | 2/4 | 4/4 | 4/4 | 4/4 | 14/16 |
| CCUG 17874 | 0/4 | 0/4 | 0/4 | 0/4 | 0/16 |
| BALB/c | | | | | |
| SPM314 | 4/4 | 4/4 | 4/4 | ND | 12/12 |
| SPM326 | 2/4 | 3/4 | 2/4 | ND | 7/12 |

With all fresh isolates the colonization was evident after the 1st week and reached an optimal level of efficiency after 4 weeks. Established strain CCUG 17874 was not able to colonize the mice.

Bacteria (Strains SPM292, 314 and 326) have been re-isolated from some infected mice and given to other mice. The efficiency of colonization was found to be increased and maximal efficiency of colonization was evident already after the first week.

Colonized mice raised an immune response against HP. This response was detected in western blot of sera of the colonized mice as described in materials and methods. There was no detectable response before the 4th week after bacterial inoculation.

Colonized mice developed a gastric pathology resembling that observed in humans. The type of gastric injury was dependent on the phenotype (cytotoxic or not-cytotoxic) of the strain employed. Non-cytotoxic strains only induced mild gastritis, while cytotoxic strains induced a more remarkable gastritis and also some epithelial erosion.

To assess the feasibility of this model for the development of HP vaccines we have immunized mice using purified HP Urease, which is considered a pivotal virulence factor for the colonization of gastric mucosa by HP. The results of these experiments are shown in Tables III–V. 80% of mice could be protected by previous immunization using LT as mucosal adjuvant.

Using a purified VacA similar results were obtained, while immunisation with H.pylori whole cell lysate resulted in 100% protection.

TABLE III

| Protection by vaccination with Urease | | |
|---|---|---|
| Treatment | infected total | % protection |
| Saline | 5/5 | 0 |
| LT | 4/5 | 20 |
| LT + Urease | 1/5 | 80 |

TABLE IV

| Protection by vaccination with VacA | | |
|---|---|---|
| Treatment | infected | % protection |
| Saline | 5/5 | 0 |
| LT | 3/4 | 25 |
| VacA | 3/4 | 25 |
| VacA + LT | 1/3 | 77 |

In the experiments reported in Tables III and IV, mice were immunized at day 1,14 and 21 with 100 µg/dose of purified H.pylori VacA plus 10 µg of LT as adjuvant. Controls consisted in groups of mice immunized orally saline alone or containing VacA alone or LT alone. At day 28, 30 and 32 they were challenged orally with strain SPM326 (cytotoxic). At day 42 mice were killed and colonization was assessed.

In the experiment shown in Table V, mice were immunized at day 0, 7 and 14 with 100 µg/dose of H.pylori antigen (VacA or urease) plus 10 µg of LT as adjuvant. Mice immunised with whole cell lysate received a $10^9$ cell equivalent of an isolate prepared from $10^{11}$ cells. Controls consisted in groups of mice immunized orally saline alone or containing LT alone. At day 21, 23 and 25 they were challenged orally with strains SPM326-2 (cytotoxic) and SPM292-2 (non-cytotoxic). At day 35 mice were killed and colonization was assessed.

These results show that by using fresh isolates of HP directly obtained from gastroduodenal patients it is possible to infect non-germ-free animals that bear normal bacterial flora. Moreover it is possible to obtain HP strains that appear to be adapted to the murine gastric environment.

TABLE V

| Protection by vaccination | | | |
|---|---|---|---|
| Treatment | infected total | % protection | No. colonies |
| Noncytotoxic bacteria (Type II) | | | |
| Saline | 8/8 | 0 | >100 |
| LT | 6/8 | 25 | >100 |
| SPM292 Lysate + LT | 0/8 | 100 | none |
| Cytotoxic bacteria (Type I) | | | |
| Saline | 14/14 | 0 | >100 |
| LT | 13/14 | 7.1 | >100 |
| VacA + LT | 3/14 | 78.6 | <5 |
| Urease + LT | 2/13 | 84.6 | <3 |

In a further experiment, different schedules of administration were applied and in particular, an intraperitoneal dose was used which allows a lower dosage to be employed. In particular, the SPM326 lysate, passaged through the mouse system provides excellent protection when combined with the MF59 adjuvant.

1. Different Schedules

6–8 week old CD1/SPF mice were fasted before each treatment as described previously. At the indicated times (see Tables VI and VII ) mice received 0.2–0.5 ml of saline containing a) 10 µg of CT, or b) a $10^9$ cell equivalent of bacterial lysates obtained as described, or c) 10 µg of CT plus a $10^9$ cell equivalent of bacterial lysates.

$10^9$ CFU of live H.pylori strains SPM292 (Table VI) or SPM326 (Table VII) were given orally, three times every 48 hour, to fasted mice at the indicated times (see Tables).

Colonization of mice was assessed 14 days after the beginning of bacterial challenge as described before.

TABLE VI

Oral immunizations: day 0, 21, 35
Bacterial challenge: day 45, 47, 49
Aassessment of infection: day 59

| Treatment | Mice/group | Infected mice | Protection |
| --- | --- | --- | --- |
| CT | 8 | 6 | 25 |
| SPM292 lysate + CT | 10 | 0 | 100 |

TABLE VII

Oral immunuzation: day 0, 14, 28
Bacterial challenge: day 35, 37, 39
Assessment of infection: day 49

| Treatment | Mice/group | Infected mice | % protection |
| --- | --- | --- | --- |
| CT | 10 | 9 | 10 |
| SPM326 lysate | 11 | 3 | 72.7 |
| SPM326 lysate + CT | 9 | 0 | 100 |

2. Different Administration Route

6–8 weeks old CD1/SPF mice, at the indicated times, received an intraperitoneal injection of 0.2 ml of saline alone or containing a) $10^9$ cell equivalent of bacterial lysate or b) $10^9$ cell equivalent of bacterial lysates plus 0.1 ml of MF59 adjuvant (1:1 final dilution).

Mice were then challenged with SPM326 H.pylori strain and the infection was assessed as described above.

TABLE VIII

Route: intraperitoneal
Immunizations: day 0, 14, 28
Bacterial challenge: day 35, 37, 39
Assessment of infection: day 49

| Treatment | Mice/group | Infected mice | % protection |
| --- | --- | --- | --- |
| saline | 6 | 6 | 0 |
| SPM326 lysate | 8 | 2 | 75 |
| SPM326 lysate + MF59 | 11 | 1 | 91 |

In a further experiment involving recombinant VacA, 6–8 weeks old CD1/SPF mice at the indicated times received an intraperitoneal injection of 0.2 ml of saline alone or containing a) 5 µg of purified VacA b) 5 µg of purified VacA plus 0.1 ml of MF59 (1:1 final dilution).

Mice were then challenged with SPM326 H.pylori strain and the infection was assessed as described above.

TABLE IX

Route: intraperitoneal
Immunizations: day 0, 14, 28
Bacterial challenge: day 35, 37, 39
Assessment of infection: day 49

| Treatment | Mice/group | Infected mice | % protection |
| --- | --- | --- | --- |
| saline | 6 | 6 | 0 |
| vacA 5 µg | 5 | 4 | 20 |
| vacA 5 µg + MF59 | 4 | 1 | 75 |

3. Recombinant Antigens, Oral Route and LT Mutant K63

The schedule and protocol of oral immunizations (days 0,7 and 14) was as described above. Fasted mice received oral immunization with a) 0.2 ml of saline containing 10 µg of LT K63, or b) 0.2 ml of saline containing 10 µg of LT K63 plus 100 µg of purified native VacA, or c) 0.2 ml of saline containing 10 µg of LT K63 plus 100 µg of purified recombinant VacA protein, p95, expressed in E.coli, or d) 0.2 ml of saline containing 10 µg of LT K63 plus 100 µg of purified recombinant Heat shock protein B (HspB) expressed in E.coli. Mice were then challenged with live H.pylori strain SPM326 as described and colonization was assessed as described previously.

TABLE X

Immunizations: days 0, 7, 14
Bacterial challenge: day 21
Assessment of infection: day 35

| Treatment | Mice/group | Infected mice | % Protection |
| --- | --- | --- | --- |
| LT K63 | 16 | 13 | 19 |
| VacA + LT K63 | 5 | 1 | 80 |
| p95 + LT K63 | 10 | 2 | 80 |
| HspB + LT K63 | 11 | 5 | 54.5 | p95 = recombinant VacA expressed in E. coli
HSpB = heat shock protein B

I claim:

1. A method for infecting a euthymic non-germ-free mouse with a human isolate of Helicobacter pylori comprising the steps of:

a) isolating Helicobacter pylori from a human patient; and b) administering a dose of a fresh isolate of Heilcobacter pylori to a euthymic non-germ-free mouse.

2. A method according to claim 1, wherein the administration of Helicobacter Pylori is repeated at 3 and 6 days after the initial infection.

3. A method according to claim 1 or claim 2 wherein, prior to the administration of Helicobacter Pylori, stomach acid is neutralised.

4. A method according to claim 1 further comprising the step of:

c) isolating Helicobacter Pylori from the euthymic mouse and administering the isolate to a further euthymic mouse.

5. A method for evaluating a vaccine against Helicobacter pylori comprising the steps of:

a) administering to a euthymic non-germ-free mouse an effective amount of candidate vaccine;

b) administering to the mouse Helicobacter pylori, in accordance with claim 1; and c) observing the incidence of Helicobacter pylori infection in the mouse.

* * * * *